United States Patent
Poon et al.

[11] Patent Number: 6,095,140
[45] Date of Patent: Aug. 1, 2000

[54] VENTILATOR TRIGGERING DEVICE

[75] Inventors: Chi-Sang Poon, Lexington; Kumaran Kolandaivelu, Brookline, both of Mass.

[73] Assignee: Massachusetts Institute of Technology, Cambridge, Mass.

[21] Appl. No.: 09/058,369

[22] Filed: Apr. 9, 1998

[51] Int. Cl.[7] .................................................. A61M 16/00
[52] U.S. Cl. ........................ 128/204.26; 128/204.23; 128/205.24; 128/204.18
[58] Field of Search .................... 128/204.26, 204.21, 128/204.24, 204.18, 205.24, 207.16, 207.12, 204.23, 203.12, 205.13, 202.22; 137/540

[56] References Cited

U.S. PATENT DOCUMENTS

| | | | |
|---|---|---|---|
| 4,213,021 | 7/1980 | Alexander | 137/450 |
| 4,362,185 | 12/1982 | Kadner | 137/540 |
| 5,042,470 | 8/1991 | Kanesaka | 128/202.22 |
| 5,050,593 | 9/1991 | Poon . | |
| 5,390,666 | 2/1995 | Kimm et al. | 128/204.26 |
| 5,520,172 | 5/1996 | Obermayer | 128/205.13 |
| 5,755,220 | 5/1998 | Ando | 128/203.12 |

FOREIGN PATENT DOCUMENTS

| | | |
|---|---|---|
| 0700687 | 3/1996 | European Pat. Off. . |
| 1449918 | 11/1966 | France . |

*Primary Examiner*—John G. Weiss
*Assistant Examiner*—V. Srivastava
*Attorney, Agent, or Firm*—Samuels, Gauthier & Stevens, LLP

[57] ABSTRACT

A device for triggering the inspiratory phase of a ventilator having a three-way connector with an inspiratory conduit and an expiratory conduit, each communicating with the ventilator and with a patient communicating conduit. A valve arrangement associated with both the expiratory and inspiratory conduits are automatically operated by a patient attempting to breathe, such that the patient is only exposed to the air volume in the three-way connector and not to the greater air volume of the ventilator and its connected tubing.

10 Claims, 4 Drawing Sheets

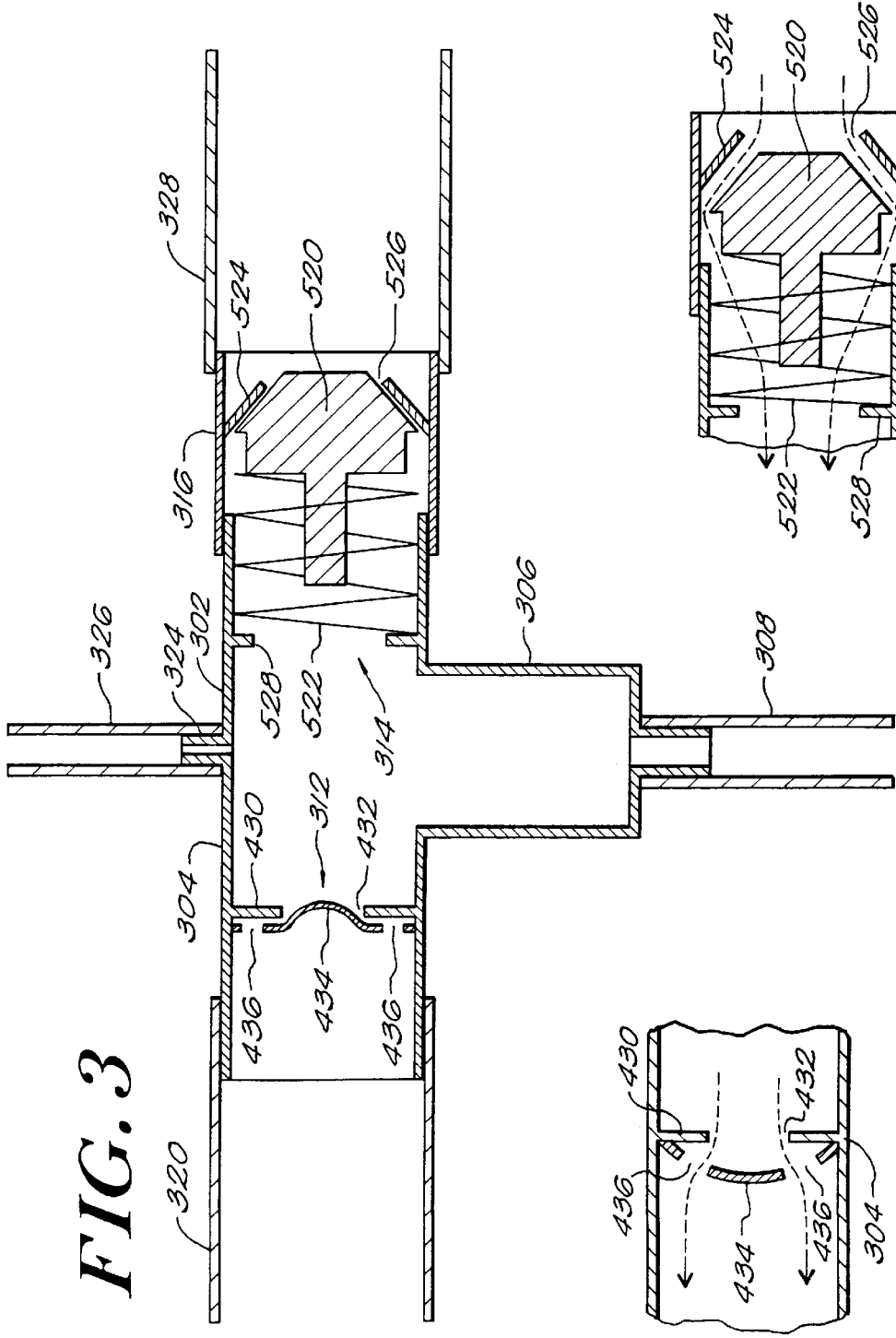

VENTILATOR TRIGGERING DEVICE

BACKGROUND OF THE INVENTION

The invention relates generally to triggering lung ventilating respirators and, more particularly, to a mechanism connecting a patient to a ventilator for initiating the respiratory phase of the ventilator.

Mechanical ventilation of the lungs is a routine life-sustaining therapy in medical intensive care units for patients suffering from respiratory failure. Most respirators in use today for this purpose are of the positive pressure type in which the lungs are inflated by a positive pressure supplied by the respirator during insufflation, followed by passive exhalation as the respirator pressure is removed, whereupon the lungs and chest will recoil from their inflated positions.

In patients who retain some spontaneous breathing activity, lung inflation may also be due in part to the patient's own respiratory efforts. In this instance, the respirator acts as a mechanical assist to the patient, partially reducing the work involved and energy expended while the patient performs the breathing.

In order to maximize the mechanical efficiency of assisted respiration and minimize the patient's risk of exposure to excessive respirator pressure, it is important to synchronize the assisting pressure of the respirator to the patient's breathing efforts. Most modern respirators are equipped with triggering systems that detect the patient's attempt to inhale, and, in response, initiate the insufflation phase. A common design detects any precipitous fall in patient airway pressure at the end of exhalation as a sign of a spontaneous inspiratory effort. As the pressure falls below a threshold level, the respirator is triggered to begin an insufflation phase. To guard against mis-triggering, the pressure threshold cannot be made too sensitive.

For the airway pressure to fall below threshold, the patient must evacuate, by his own active inspiratory efforts, a sizable volume from the respiratory circuit which includes the respirator tubings, connectors, passageway, humidifier and accessories which may be associated with them. In those patients with stiff lungs and small lung capacities (e.g., infants with hyaline membrane disease), the inspiratory effort required to trigger the respirator may become prohibitive, especially if the evacuation volume in the inspiratory circuit is relatively large compared to the capacity of their lungs. Thus, inspiratory triggering by such patients is often difficult, if at all possible.

Prior attempts in overcoming these problems have included various means of detecting chest wall movement or air flow near the airway opening using plethysmographic methods or flow transducers, respectively. Thus, lung expansion, instead of airway pressure, is used as the triggering signal. These approaches require relatively elaborate instrumentation that is cumbersome, costly, and difficult to operate. Bulky and delicate volume or flow sensors must be attached directly to the patient. None of these methods have been proven effective in allowing sensitive and reliable inspiratory triggering.

Ideally, an inspiratory triggering device should be sensitive enough to provide the desired triggering with minimum encumbrance to the patient, and yet simple enough to be relatively light-weight, flexible and low-cost. Furthermore, it should not adversely affect the well being of the patient or cause unnecessary inconvenience to the therapist in its operation. Such a device is presently lacking.

On the other hand, an advantage of pressure triggering is that a pressure signal can be readily obtained by way of a side tap to the respiratory circuit proximal to the patient while direct attachment of the pressure transducer to the patient is not necessary. Its disadvantage, however, as used in current practice, is that the airway pressure that provides the trigger can be greatly attenuated in the presence of a large evacuation volume in the respiratory circuit. Apparatus that eliminates or minimizes the effect of the evaluation volume would be useful in providing sensitive pressure triggering and hence, an object of the present invention.

SUMMARY OF THE INVENTION

The invention provides a triggering device for initiating an inspiratory phase of either pressure driven or continuous flow ventilators. In each variation, the design consists of a three way connector which has an inspiratory conduit and an expiratory conduit and a patient connection.

In the pressure driven ventilatory method, both the inspiratory and expiratory conduits are in communication with the respirator. In the continuous flow variation, these lines lead to a common junction with the high flow line, from which the patient inhales and exhales into.

A one way valve is associated with the expiratory conduit to permit air (breath) flow only to the respirator or high flow junction (depending on variation) and not from it. A variable cracking pressure check valve is associated with the inspiratory conduit to selectively permit air flow from the respirator or high flow line (depending on the variation) to the patient. By adjusting the cracking pressure, the trigger sensitivity (TS) can be adjusted, and compensations for positive end expiratory pressures (PEEP)can be made (cracking pressure=TS+PEEP).

An air tap in the patient communicating conduit is connected to the respirator and when it detects a pressure change in the patient communicating tube of the three-way conduit, it triggers the respirator. Additionally, in the continuous flow variation, when the three-way conduit pressure equals the cracking pressure, the patient can begin to inspire from the high flow line prior to ventilator assist, whereupon the ventilator takes on the patient's work of breathing and the work needed to retain the open check valve.

Thus, the one-way valve in the expiratory conduit is a first closure valve and the check valve associated with the inspiratory conduit is a second closure valve. Together, when closed, they isolate the patient from the air volume associated with the respirator and those tubes communicating with it. The patient is thus exposed only to the air volume of the three-way connector.

The above and other features of the invention, including the various novel details combination of parts, will now be more particularly described with reference to the accompanying drawings and pointed out in the claims.

BRIEF DESCRIPTION OF THE DRAWINGS

FIG. 3 is a sectional view on an enlarge scale of the device shown at the time of post expiration and inspiratory occlusion, when both the inspiratory valve and expiratory valves are in closed position;

FIG. 4 is an enlarged, sectional detailed view of the expiratory valve on the open position, indicating air flow;

FIG. 5 is an enlarged, sectional view of the inspiratory valve in the open position, indicating air flow.

DETAILED DESCRIPTION OF THE ILLUSTRATED EMBODIMENTS

Figure 1:
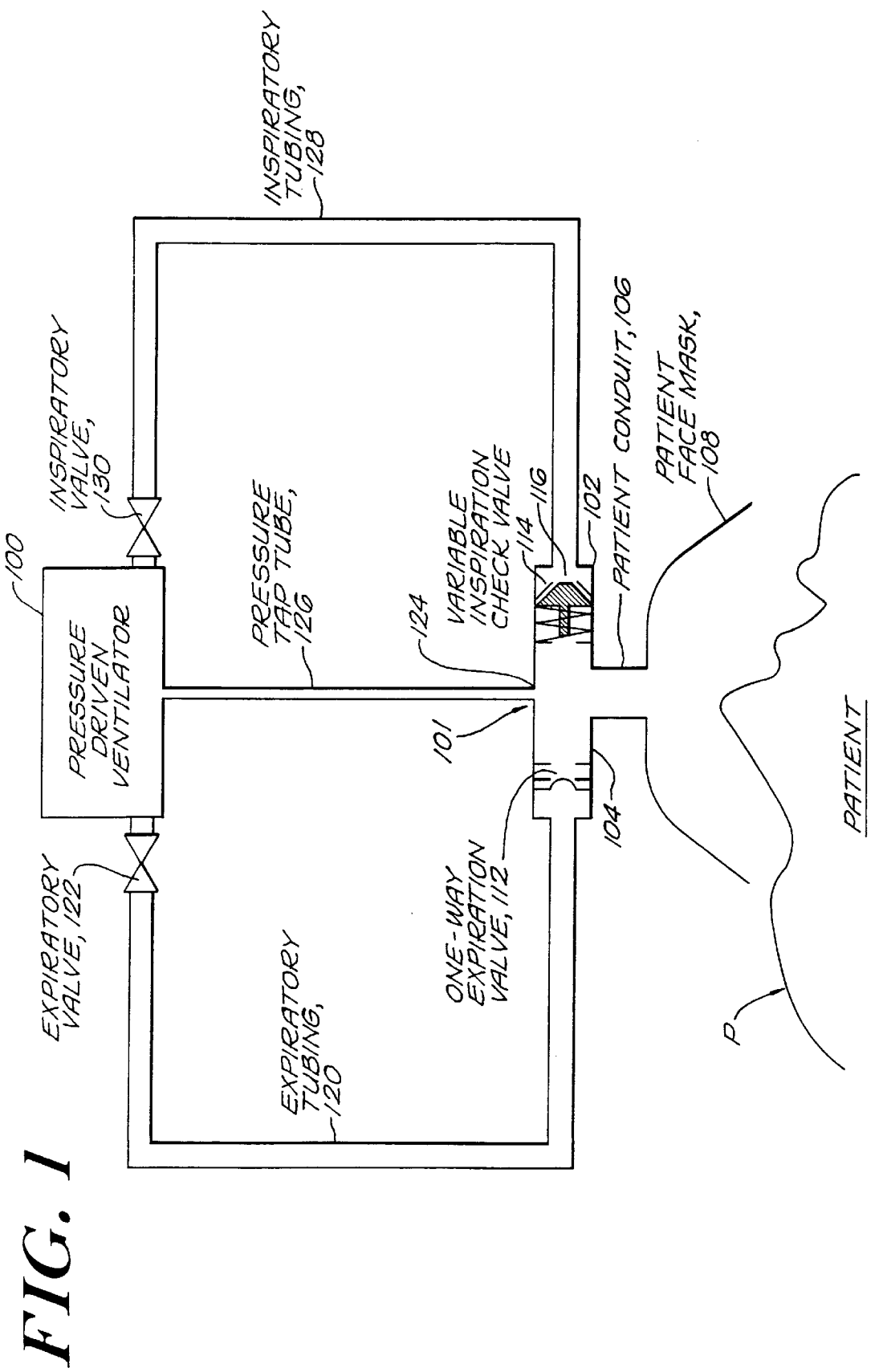
FIG. 1 is a schematic view, partly in section, of a respirator triggering device embodying the invention and shown connecting a patient to a pressure driven respirator.

FIG. 1 schematically shows the triggering device embodying the invention connecting a patient P to a pressure driven ventilator 100. A three-way connector 101, has an inspiratory conduit 102 and expiratory conduit 104, each in communication with a patient connecting conduit 106 and the ventilator. The three-way connector may be made of polystyrene, polypropylene, polycarbonate or any other surgically acceptable material. Wherein a facial mask 108 is shown, a tracheal tube alone could also be employed if conditions dictated.

A one-way closure or expiratory valve 112 is associated with the expiratory conduit 104 to permit air (breath) flow only to the ventilator, as shown by an arrow, through an expiratory tube 120. An expiratory valve 122 couples the expiratory tube to the ventilator.

A variable inspiratory check valve generally designated 114, is associated with the inspiratory conduit 102 to selectively permit air flow from the ventilator to the patient. A pressure chamber 116 surrounds the inspiratory valve 114 and operates to open and close the valve in response to pressure change in the expiratory conduit 104 (or anywhere in the three-way connector 101) by the patient attempting to breathe. A side tap 124, which may also be called a pressure tap or air tap, in the patient conduit 106, is a hollow tube in an opening in the patient conduit 106 which is connected to the ventilator by a flexible tube 126, allows the detection of airway pressure of the patient. The side tap 124 may be located any place in the three-way connector C within the confines of the valves 112 and 114. The variable inspiration check valve 114 is coupled to the ventilator through an inspiratory tube 128 and an inspiratory valve 130.

Figure 2:
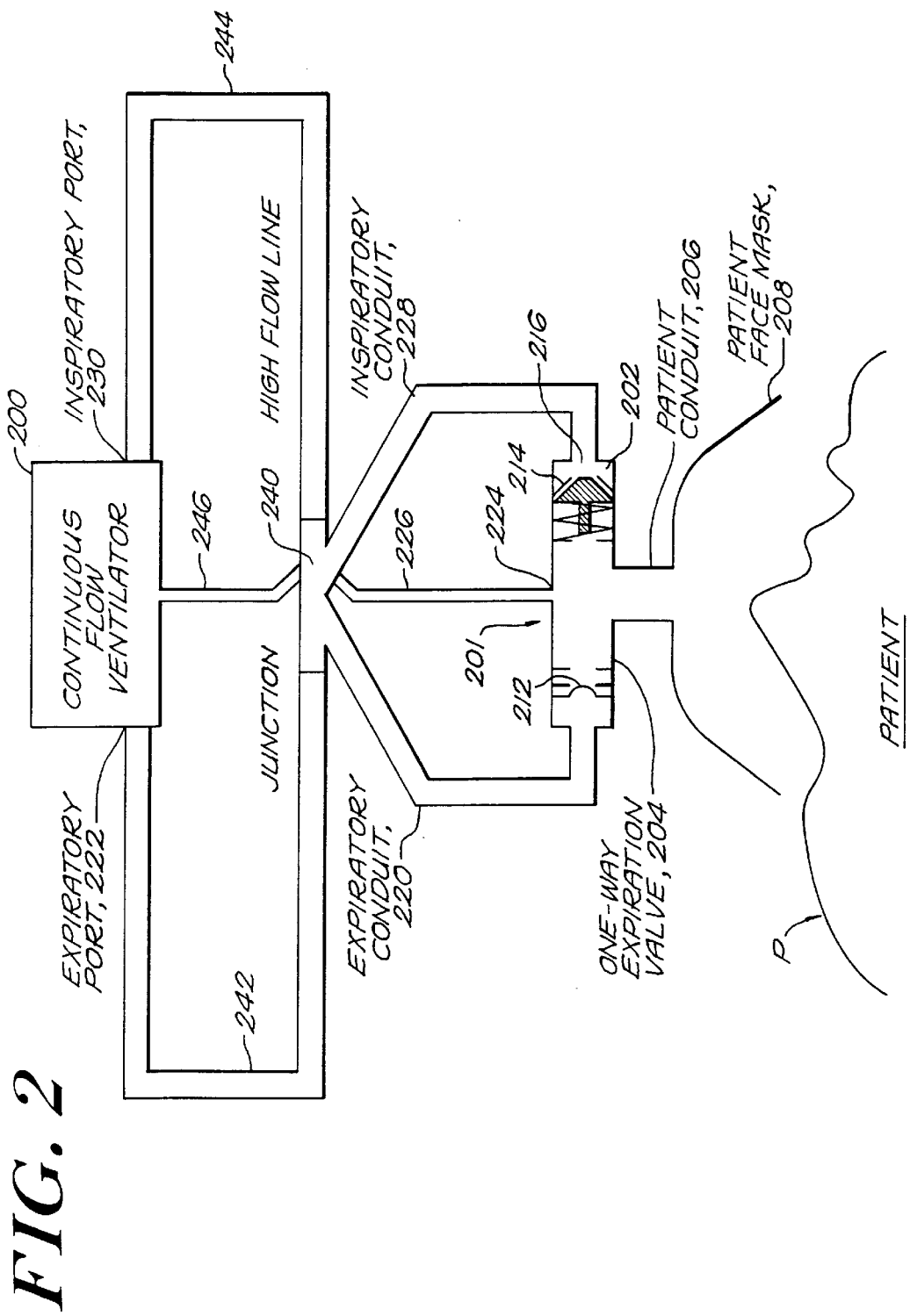
FIG. 2 is a schematic view, partly in section, of a respirator triggering device embodying the invention and shown connecting a patient to a continuous flow ventilator.

FIG. 2 is a schematic view, partly in section, of a respirator triggering device embodying the invention and shown connecting a patient to a continuous flow ventilator.

FIG. 3 is a sectional view on an enlarged scale of the device shown at the time of post expiration and inspiratory occlusion, when both the inspiratory valve 314 and expiratory valves 312 are in a closed position. The inspiratory conduit 302 is in communication with the inspiratory valve outer casing 316 which in turn communicates with the inspiratory tubing 328. The expiratory conduit 304 is connected to the expiratory tubing 320. Both inspiratory and expiratory conduits are in communication with the patient connecting conduit 306 which leads to tubing 308. This tubing can lead to a facial mask, as shown in FIGS. 1 and 2 or to a tracheal tube, as conditions dictate. A pressure tap 324 and tubing 326 are coupled to the ventilator.

FIG. 4 is an enlarged, sectional detailed view of the expiratory valve 312 in the open position, indicating air flow. The one-way closure expiratory valve 312 permits air (breath) flow only to the ventilator or continuous flow line, as shown by the dashed arrows. The valve operates by the pressure differential (from right to left) across a diaphragm 434. In the closed position (zero or negative pressure differential) the diaphragm 434 is pressed against an annular plastic disc 430 secured to the inner walls of the expiratory conduit 304 as shown in FIG. 3. When the pressure differential becomes positive, as during expiration, air moves through the central aperture 432 of the disc 430 causing the diaphragm to bulge outwardly to the left, as seen in FIG. 4, whereupon the air then exits through the apertures 436 in the membrane. This valve is merely illustrative of one-way valves. Any equivalent valve may be employed.

FIG. 5 is an enlarged, sectional view of the inspiratory valve 314 in the open position, indicating air flow. The inspiratory check valve 314 permits air flow only to the patient as shown by the dashed arrows when the pressure differential from right to left is greater than the cracking pressure as determined by a compressional spring 522 and its initial compression. At this time a plunger 520, which otherwise creates a seal with the conical aperture 524, is displaced to the left permitting the air flow. The initial compression is dependent on the uncompressed length of the spring 522, and the boundary positions in the closed state shown in FIG. 3.

The left boundary position is defined by an annular plastic disc 528 which holds the left end of the spring 522 stationary. The right boundary position is determined by the relative position of the inspiratory valve outer casing 316 and the inspiratory conduit 302. By moving the outer casing 316 to the right, the initial compression is decreased, decreasing the cracking pressure accordingly. Conversely, a leftward displacement of the outer casing 316 with respect to the inspiratory conduit 302 would create an increased initial compression and cracking pressure.

The triggering device operates in the following manner with the pressure driven ventilator system shown in FIG. 1. During the expiratory phase of the patient's breathing cycle, the expiratory valve 122 of the ventilator 100 is open while the corresponding inspiratory valve 130 is closed. This results in no air flowing from the respirator to the patient via the inspiratory tubing 328. However, the expiratory tubing 320 is then open to the ventilator. The patient exhales through the face mask (or tracheal tube), the conduit 304 and thence through the aperture 432 of the annular one-way valve 312 and then through the perforations 436 of the elastomeric diaphragm 434.

Figure 6:
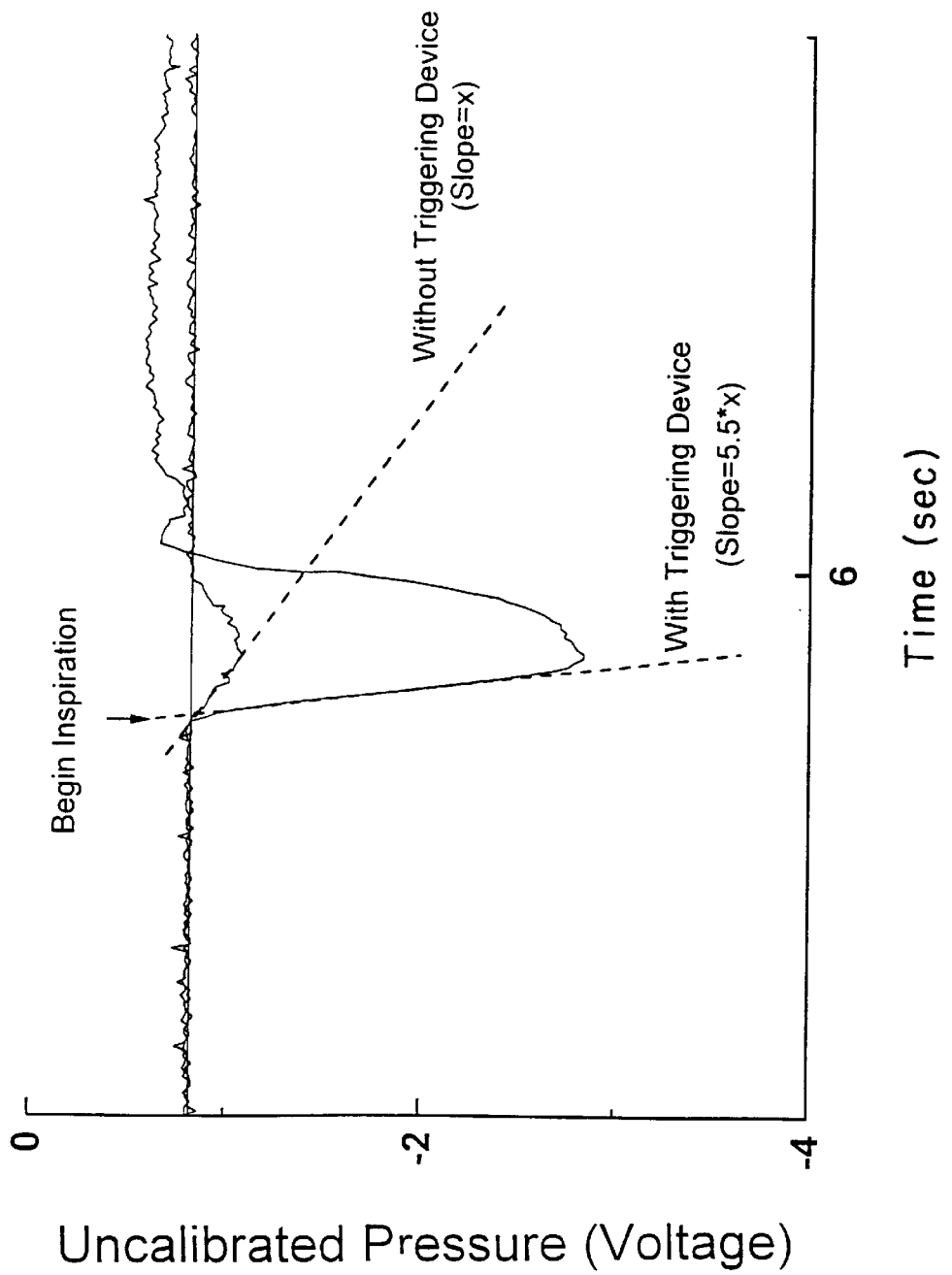
FIG. 6 is a plot showing the rise rate and magnitude of the pressure signal obtained with a prototype triggering device in comparison with that obtained with no mechanism. In these examples, the inspiratory and expiratory tubings are open to atmosphere in a worst case scenario.

Shortly after expiration, all of the inspiratory 130,314 and expiratory 122,312 valves close, and no flow occurs. This condition is present at the beginning of patient inspiratory drive, thus shielding the patient from large gas volume in the expiratory and inspiratory conduit. Therefore, the pressure in the three-way junction quickly drops upon inspiration as seen in FIG. 6. FIG. 6 is a plot showing the rise rate and magnitude of the pressure signal obtained with a prototype triggering device in comparison with that obtained with no mechanism. In these examples, the inspiratory and expiratory tubings are open to atmosphere in a worst case scenario.

This pressure is communicated to the ventilator via the pressure tap 324 and tubing 326, both of which are of small diameter. This pressure can be used to signal the ventilator to open its inspiratory valve 130, sending a positive pressure head through the inspiratory tubing 328, and opening the inspiratory valve 314 by displacing the plunger 520 to the left. This creates inspiratory flow which travels through the inspiratory tubing, through the aperture 526, through the outer casing 316 and the inspiratory conduit 302 and to the patient via the patient conduit 306 and connecting tubing 308. This flow is diverted from the expiratory tubing 320 as the expiratory valve on the ventilator is closed.

By minimizing the cracking pressure (in accordance with the ventilator trigger sensitivity) the system can be optimized in terms of extra-ventilator work needed to hold the inspiratory valve open.

The triggering device operates in the following manner with the continuous flow ventilator system shown in FIG. 2. During the expiratory phase, there is nominal continuous flow in the ventilator circuit from the inspiratory 230 to the expiratory 222 ports. The patient exhales through the face mask 208 (or tracheal tube), the conduit 304 and thence through the aperture 432 of the annular one-way valve 312 and then through the perforations 436 of the elastomeric diaphragm 434. This flow continues through the expiratory tubing 320 and joins the continuous flow track at the junction 240, where it joins the nominal flow and travels to the ventilator where it is released. Throughout this phase, the device's inspiratory valve remains closed and there is no flow through the inspiratory tubing 328.

Shortly after expiration, all of the inspiratory and expiratory valves are closed, and patient/ventilator communication occurs. This condition is present at the beginning of patient inspiratory drive thus, shielding the patient from the volumes of the inspiratory 328 and expiratory 320 tubing, and the continuous flow of the ventilator. Therefore, the pressure in the three-way junction quickly drops with patient inspiratory effort. This pressure is communicated to the ventilator via the pressure tap 324 and tubing 326, both of which are of small diameter. The pressure can be used to signal the ventilator to increase its inspiratory flow.

By narrowing the expiration port, the flow is diverted to the triggering device's inspiratory tubing 328 and opens the inspiratory valve 314 by displacing the plunger 520 to the right. The flow continues through the aperture 526, through the outer casing 316 and the inspiratory conduit 302 and to the patient via the patient conduit 306 and connecting tubing 308. This flow is diverted from the expiratory tubing 320 since as the pressure in the inspiration tubing 328 increases, so does that in the expiratory tubing, as they connect to the continuous flow line at a common junction 240. Additionally, as the flow travels through the inspiration valve, there is a pressure loss due to the cracking pressure and resistance of the valve. This creates the negative pressure differential across the expiration diaphragm 434 during inspiration, closing the expiratory valve.

By minimizing the cracking pressure (in accordance with the ventilator trigger sensitivity) the system can be optimized in terms of extra-ventilator work needed to hold the inspiratory valve open. Additionally, as the cracking pressure tends to zero, the system tends to continuous communication between the patient and ventilator.

The foregoing description has been set forth to illustrate the invention and is not intended to be limiting. Since modifications of the described embodiments incorporating the spirit and substance of the invention may occur to persons skilled in the art, the scope of the invention should be limited solely with reference to the appended claims and equivalents thereof.

What is claimed is:

1. A system for triggering insufflation by a pressure-driven or continuous-flow ventilator comprising:
   a) a connector including:
      i) an inspiratory conduit which is coupled to an inspiratory valve of the ventilator,
      ii) an expiratory conduit which is coupled to an expiratory valve of the ventilator, and
      iii) a patient-connecting conduit which is coupled to a breathing passage of a patient;
   b) a one-way expiratory valve disposed in the expiratory conduit which is moveable from a closed position to an open position responsive to exhalation of the patient through the patient-connecting conduit, whereby the patient's breath passes through the one-way expiratory valve to the ventilator when the respirator is in an expiratory mode;
   c) a variable pressure inspiratory check valve disposed in the inspiratory conduit, said inspiratory check valve including means for adjusting the valve cracking pressure to selectively allow said inspiratory check valve to be moveable between an open position, wherein fluid communication is provided between the patient-connecting conduit and the inspiratory valve, and a closed position, wherein the inspiratory check valve seals the patient-connecting conduit from the inspiratory valve, for both pressure-driven flow and continuous flow; and
   d) an air tap disposed at a portion of the connector which is between the one-way expiratory valve and the inspiratory check valve and which is coupled to the ventilator, and responsive to voluntary inhalation by the patient to move the one-way expiratory valve and the inspiratory check valve from their open positions to their closed positions to cause pressure within the connector and in the air tap to diminish in an amount sufficient to trigger the ventilator to shift from an expiratory mode to an inspiratory mode, in which the expiratory valve closes and the inspiratory valve opens, and in which air is directed from the ventilator through the inspiratory valve to force the inspiratory check valve from the closed position to the open position, thereby causing insufflation of the patient by the ventilator.

2. The system of claim 1, wherein said inspiratory check valve comprises a spring loaded plunger which interacts with an aperture and is moveable between open and closed positions to provide fluid communication between the patient-connecting conduit and the inspiratory valve when the plunger is in the open position, and to seal the patient-connecting conduit from the inspiratory valve when the plunger is in the closed position.

3. The system of claim 2, wherein said adjusting means comprises an outer casing on said inspiratory conduit which is moveable so as to compress and expand the interaction between said plunger and said aperture.

4. The system of claim 3, wherein said adjusting means is utilized to adjust trigger sensitivity and making compensations for positive end expiratory pressures.

5. The system of claim 3, wherein said one-way expiratory valve includes an apertured diaphragm engageable with an apertured disc.

6. The system of claim 1, wherein said ventilator comprises a pressure driven ventilator.

7. The system of claim 1, wherein said ventilator comprises a continuous flow ventilator.

8. The system of claim 7, wherein said inspiratory and expiratory conduits and said air tap are coupled to said ventilator through a high flow junction.

9. The system of claim 8, wherein said high flow junction is coupled to said ventilator through a high flow inspiratory line, an expiratory line and a tap line.

10. The system of claim 8, wherein in response to the pressure in said connector being equal to being equal to said cracking pressure, said ventilator assists patient breathing and retaining said inspiratory check valve open.

* * * * *